United States Patent
Wright et al.

(10) Patent No.: US 8,433,544 B2
(45) Date of Patent: Apr. 30, 2013

(54) NONLINEAR VARIABLE LAG SMOOTHER

(75) Inventors: James R. Wright, Morgantown, PA (US); James William Woodburn, Ardmore, PA (US)

(73) Assignee: Analytical Graphics Inc., Exton, PA (US)

( * ) Notice: Subject to any disclaimer, the term of this patent is extended or adjusted under 35 U.S.C. 154(b) by 788 days.

(21) Appl. No.: 12/343,948

(22) Filed: Dec. 24, 2008

(65) Prior Publication Data

US 2010/0161284 A1 Jun. 24, 2010

Related U.S. Application Data

(60) Provisional application No. 61/140,665, filed on Dec. 24, 2008.

(51) Int. Cl.
*G06F 3/00* (2006.01)
*G06F 3/01* (2006.01)
*G06F 3/03* (2006.01)
*G06F 3/05* (2006.01)

(52) U.S. Cl.
USPC ............ 702/190; 702/179; 702/181; 702/189

(58) Field of Classification Search .................. 702/141, 702/142, 176, 178, 179, 181, 189, 190; 342/357.23; 455/456.1
See application file for complete search history.

(56) References Cited

U.S. PATENT DOCUMENTS

| | | | | |
|---|---|---|---|---|
| 5,416,712 | A * | 5/1995 | Geier et al. ............... 701/472 |
| 6,724,343 | B2 * | 4/2004 | Asher et al. .............. 342/357.23 |
| 7,177,653 | B2 * | 2/2007 | McAvoy .................. 455/456.1 |
| 7,373,252 | B2 * | 5/2008 | Sherrill et al. ................ 702/17 |
| 7,439,908 | B1 * | 10/2008 | Zhodzishky et al. ... 342/357.24 |
| 7,536,262 | B2 * | 5/2009 | Hornbostel et al. ............ 702/17 |
| 2008/0165053 | A1 * | 7/2008 | Liu et al. .................. 342/357.03 |

OTHER PUBLICATIONS

R.E. Kalman, "New Methods in Wiener Filtering Theory," Research Mathematics, Research Institute of Applied Science, 1963, pp. 270-388.

Kristine Larson & Judah Levine, "Time Transfer Using the Phase of the GPS Carrier," IEEE Transactions on Ultrasonics, Ferroelectrics, & Frequency Control, vol. 45, No. 3, May 1998, pp. 539-540.

Kristine Larson & Judah Levine, "Carrier-Phase Time Transfer," IEEE Transactions on Ultrasonics, Ferroelectrics, & Frequency Control, vol. 46, No. 4, Jul. 1999, pp. 1001-1012.

Kristine Larson, Judah Levine, Lisa Nelson, & Thomas Parker, "Assessment of GPS Carrier-Phase Stability for Time Transfer Applications," IEEE Transactions on Ultrasonics, Ferroelectrics, & Frequency Control, vol. 47, No. 2, Mar. 2000, pp. 484-494.

J.S. Meditch, "Stochastic Optimal Linear Estimation & Control," McGraw-Hill Book Company, 1969, pp. 231-234.

James Meditch, "Orthogonal Projection & Discrete Optimal Linear Smoothing," J. SIAM Control, vol. 5, No. 1, 1967, pp. 74-89.

(Continued)

*Primary Examiner* — Eliseo Ramos Feliciano
*Assistant Examiner* — Felix Suarez
(74) *Attorney, Agent, or Firm* — The Marbury Law Group, PLLC (57) ABSTRACT

An extended Kalman filter (EKF) is combined with a fixed epoch smoother (FES) to produce a new variable lag smoother (VLS). The fixed epoch lags EKF measurement time-tags with variable time lag. The combination of EKF and FES is referred to herein as a variable lag smoother (VLS).

20 Claims, 4 Drawing Sheets

OTHER PUBLICATIONS

J.S. Meditch, "Survey of Data Smoothing for Linear & Nonlinear Dynamic Systems," Automatica, vol. 9, 1973, pp. 151-162.

H.E. Rauch, "Solutions to the Linear Smoothing Problem," IEEE Transactions on Automatic Control, Short Papers, Oct. 1963, pp. 371-372.

H.E. Rauch, F. Tung, C.T. Striebel, "Maximum Likelihood Estimates of Linear Dynamic Systems," AIAA Journal, vol. 3, No. 8, Aug. 1965, pp. 1445-1450.

S. Sherman, "Theorem on Convex Sets with Applications," The Annals of Mathematical Statistics, vol. 26, No. 4, Dec. 1955, pp. 763-767.

Seymour Sherman, "Non-Mean Square Error Criteria," IEEE Transactions on Information Theory, Sep. 1958, pp. 125-126.

J.R. Wright, "Sequential Orbit Determination with Auto-Correlated Gravity Modeling Errors," Journal of Guidance & Control, vol. 4, No. 3, May-Jun. 1981, pp. 304-309.

James R. Wright, "Orbit Determination Solution to Non-Markov Gravity Error Problem," AAS/AIAA Spaceflight Mechanics Meeting, Cocoa Beach, FL, Feb. 14-16, 1994, pp. 1-20.

James R. Wright, "Optimal Orbit Determination," American Astronautical Society, 2002, pp. 1-12.

James R. Wright, "Real-Time Estimation of Local Atmospheric Density," AAS/AIAA, 2003, pp. 1-22.

James R. Wright & James Woodburn, "Simultaneous Real-Time Estimation of Atmospheric Density & Ballistic Coefficient," Paper AAS 04-175, AAS/AIAA, Feb. 1, 2004, pp. 1-29.

Sergei Tanygin & James R. Wright, "Removal of Arbitrary Discontinuities in Atmospheric Density Modeling," Paper AAS 04-176, AAS/AIAA, Feb. 2, 2004, pp. 1-12.

James R. Wright, "Sherman's Theorem," The Journal of the Astronautical Sciences, vol. 54, Nos. 3 & 4, Jul.-Dec. 2006, pp. 299-319.

James R. Wright, "Composite Clocks Three-State Models," 39th Annual Precise Time and Time Interval Systems and Applications Meeting, Long Beach, CA, Nov. 2007, pp. 1-18.

James R. Wright, "GPS Composite Clock Analysis," International Journal of Navigation and Observation, vol. 2008, Article ID 261384, Nov. 2007, pp. 1-8.

James R. Wright, James Woodburn, Son Truong, William Chuba, "Orbit Gravity Error Covariance," Paper AAS 08-157, Jan. 2008, pp. 1-19.

James R. Wright, James Woodburn, Son Truong, William Chuba, "Sample Orbit Covariance Function & Filter Smoother Consistency Tests," Paper AAS 08-159, Jan. 2008, pp. 1-19.

James R. Wright, James Woodburn, Son Truong, William Chuba, "Orbit Covariance Inner Integrals with Polynomials," Paper AAS 08-161, Jan. 2008, pp. 1-12.

James R. Wright, James Woodburn, "Nonlinear Variable Lag Smoother," Paper AAS 08-303, Jul. 2008, pp. 1-20.

* cited by examiner

NONLINEAR VARIABLE LAG SMOOTHER

CROSS REFERENCE TO RELATED APPLICATIONS

This application claims the benefit of Provisional Application No. 61/140,665 filed Dec. 24, 2008. The 61/140,665 application is incorporated by reference herein, in its entirety, for all purposes.

BACKGROUND AND SUMMARY

For ease of discussion, the follow abbreviations are used herein: EKF for extended Kalman filter, FIS for fixed-interval smoother, FES for fixed-epoch smoother, SP for sequential processing, LS for least squares, IOD for initial orbit determination, RMS for root mean square, and VLS for variable-lag smoother.

Nonlinear multidimensional estimation problems require the use of nonlinear multidimensional estimation systems. Nonlinear estimation systems process measurements to estimate dynamical system states, and dynamical system states are driven by force models. All measurements have measurement errors, and all force models have force model errors. Thus all state estimates have estimation errors. One object of an estimation system is to calculate optimal state estimates—that is, state estimates with smallest estimation errors. Given no a priori state estimate, then a sequence of estimators must be applied to calculate an optimal multidimensional state estimate.

First an initial state estimate must be calculated using a nonlinear iterative technique. Every initial state estimate has very large estimation errors because the estimation problem is multidimensional and nonlinear, and because there does not exist an a priori state estimate to be refined since the state is completely unknown.

Given an initial state estimate with large estimation errors, the initial state estimate is input to the method of iterative least squares to generate a least squares state estimate, thereby producing a refined least squares state estimate with significantly reduced state estimate errors.

Given a refined least squares state estimate with sufficiently small state estimate errors, the least squares state estimate is used, together with an ad-hoc state estimate error covariance matrix, to initialize an optimal sequential real-time filter. The filter is then used to process measurements sequentially until the filter state estimate is fully initialized, after which the covariance matrix may be said to be realistic. Thereafter the filter is optimal in real time. Optimal predicted state estimates can be calculated from optimal filtered state estimates.

The user may trade the filter real time capability for state estimate accuracy improvement, by accepting state estimate time lag. For this purpose, during execution of the real-time filter, all filter calculations are saved for later use in a fixed-interval smoother (FIS). The user decides when to terminate the real-time filter run, and uses the filter state estimate and covariance to initialize an FIS. Using quantities calculated during the filter execution, the FIS is executed backwards in time to generate smoothed estimates with better accuracy than filtered estimates at the same times. The FIS also creates an FIS state estimate error covariance matrix with each FIS state estimate.

Spacecraft orbit determination provides an illustrative example of a nonlinear multi-dimensional orbit estimation problem with significant measurement errors and significant force modeling errors. The state estimate always contains six parameters for the orbit, one or more parameters for measurement biases, and various force model parameters. Specifically, the state estimate of a low Earth orbit (LEO) spacecraft comprises three components of spacecraft position, three components of spacecraft velocity, atmospheric density, ballistic coefficient, and measurement biases. By way of illustration and not as a limitation, other state parameters may include photon solar pressure, clock biases, spacecraft maneuver parameters, albedo acceleration, troposphere bias, ionosphere biases, station location biases, antenna phase center biases, and multi-path biases. The six components of spacecraft position and velocity are called the "orbit." The general problem for orbit determination is first to estimate an initial orbit estimate, and thereafter to estimate corrections to previous state estimates using new measurements.

Currently estimators used for orbit determination involve an initial orbit determination (IOD), batch least squares differential corrections (LS), and sequential processing (SP). Operationally, the order in which these methods are used defines a functionally dependent sequence: An orbit estimate output from IOD can be used as orbit estimate input to initialize LS, and an orbit estimate output from LS can be used as orbit estimate input to initialize SP.

IOD methods input tracking measurements with tracking platform locations, and output spacecraft orbit estimates. No a priori orbit estimate is required, and when used, it is assumed that no a priori orbit estimate exists. Associated output orbit estimation error magnitudes are very large. IOD methods are nonlinear and six-dimensional. Refined measurement residual editing is not possible during IOD calculations because no a priori orbit estimate exists.

LS methods input tracking measurements with tracking platform locations and an a priori orbit estimate, and output a refined orbit estimate. An a priori orbit estimate is required. Associated output error magnitudes are small when compared to IOD outputs. LS methods consist of a sequence of linear LS corrections where sequence convergence is defined as a function of tracking measurement residual RMS (Root Mean Square). Each linear LS correction is characterized by a minimization of the sum of squares of tracking measurement residuals. LS methods produce refined orbit estimates in a batch mode, together with error covariance matrices that are optimistic. That is, LS orbit element error variance estimates are typically too small, relative to truth, by at least an order of magnitude. All LS methods require an inversion of an n×n LS information matrix for each LS iteration, where n is state estimate size. This is problematic when the information matrix is ill-conditioned. The information matrix is frequently ill-conditioned for orbit determination applications of LS. Operationally, LS may be the only method used, or it may be used to initialize SP. The existence of an a priori orbit estimate enables operational measurement residual editing, but LS methods frequently require inspection and manual measurement editing by human intervention. LS algorithms therefore require elaborate software mechanisms for measurement editing.

SP methods input tracking measurements with tracking platform locations, input an a priori state estimate (inclusive of orbit estimate), and input an a priori state error covariance matrix. An a priori state estimate is required, and an a priori state error covariance matrix is required. SP methods output refined state estimates in a sequential mode. SP filter methods are forward-time recursive sequential machines consisting of a repeating pattern of filter time update of the state estimate and filter measurement update of the state estimate. The filter time update propagates the state estimate forward, and the filter measurement update incorporates the next measurement. The recursive pattern includes an important interval of filter initialization. No state-sized matrix inversions are performed during filter calculations. The fixed-interval smoother (FIS) is a backward-time recursive sequential machine consisting of a repeating pattern of state estimate refinement using filter outputs and backwards transition. Matrix inversions are required by the FIS algorithm. Time transitions for both filter and smoother are CPU-dominated by numerical orbit propagations and state matrix multiply calculations.

In summary, IOD methods produce crude state estimates from measurements alone, whereas LS and SP methods produce refined corrections to a priori state estimates.

Measurement data consist of two additive unknown components: signal and noise. The signal is the unknown time-varying measurement component of interest. The noise is a random unknown time-varying functional that partially obscures the signal. The unknown true state is a function of the signal but not the noise. Thus every state estimate derived from measurements has state estimate errors due to measurement noise.

As an example, consider the measurement of the right ascension and declination angles of a telescope boresight that tracks celestial objects and/or spacecraft. Measurement noise is an additive composition of random white noise and random serially-correlated time-varying biases. Range and Doppler spacecraft measurements are derived from electronic hardware that consists of transmitters, receivers, transceivers, transponders, and other components. For GPS measurements, transmitters are deployed on GPS NAVSTAR spacecraft and receivers are deployed on USER spacecraft. Every component of electronic hardware produces random thermal noise (white noise) due to circuit resistance phenomena related to dynamics of electrons in the circuit. Random serially-correlated time-varying biases derive from clock phenomenology used in transmitters and receivers to create the range and Doppler measurements.

The forces applied to the satellite are modeled. For example, gravity models, atmospheric density models, ballistic models, solar photon pressure models, spacecraft surface description models, and thrust models are used in numerical orbit propagations to estimate the state of a LEO spacecraft. Because force models are inexact, the force models have errors and the state estimates they produce have errors.

As previously noted, a fixed-interval smoother (FIS) multi-dimensional nonlinear estimator uses a set of filter outputs. These filter outputs are stored while running the filter for later use in the FIS. The last filter output is used to initialize the FIS is the first smoother input. The filter runs forward with time. The FIS runs backwards with time. This incurs a significant operational throughput delay.

In an embodiment of a nonlinear multi-dimensional fixed-epoch smoother (FES), each FES is initialized by the EKF when the EKF reaches the fixed epoch specified by the user. The EKF processes measurements, but the FES does not process measurements. Rather, each FES moves measurement information, derived from the forward moving EKF state estimate, backwards to a fixed epoch. Each FES state estimate lags real-time.

In an embodiment, an extended Kalman filter (EKF) is combined with a fixed epoch smoother (FES) to produce a new variable lag smoother (VLS). The fixed epoch lags EKF measurement time-tags with variable time lag. The combination of EKF and FES is referred to herein as a variable lag smoother (VLS).

Described herein are two embodiments, a Fraser embodiment (FES/F), and a Carlton-Rauch embodiment (FES/CR).

The FES/F does not require a state-sized matrix inverse calculation. The FES/CR requires the calculation of a state-sized covariance matrix inverse for each FES/CR execution. However, this is not meant as a limitation. Other FESs may be used in combination with various filters to produce a variable lag smoother providing the functionality described herein.

DETAILED DESCRIPTION

In the discussion that follows, "Class A" denotes a class of linear optimal sequential estimators and "Class Ã" denotes a class of non-linear optimal sequential estimators that derive from the linear estimators of class A by extension. Class Ǎ denotes the union of classes A and Ã. For prototype in Class Ã we have the well-known extended Kalman filter (EKF). Epoch for the KF and EKF is defined by the time-tag $t_k$ of the last measurement processed, or by propagation to $t_{k+1} > t_k$. But the epoch for each VLS state estimate of interest lags the time-tag $t_k$ of last measurement processed by the EKF. The state estimate error magnitude is always smallest, thus accuracy is best, at estimation epoch for each member of Class A. But each smoothed state estimate has better accuracy than a filtered state estimate, at the same epoch, when the smoothed state estimate epoch lags EKF measurement time-tags with a significant time-lag. Here the smoother has processed more measurements than the filter, and the smoother estimate derives from information forward of the smoother epoch and from information prior to the smoother epoch, whereas the filter estimate derives only from information prior to the same epoch.

There exists a class of nonlinear estimation problems that cannot be solved with a real-time EKF alone because all tracking data precedes the real-time EKF state epoch, and tracking data following the real-time EKF state epoch are not available. An example is provided by the problem of estimating the velocity change due to an impulsive maneuver at the time of maneuver impulse. The most accurate state estimate must use tracking data both before and after the time of maneuver impulse. This is enabled with VLS. A second example is provided by the optimal simultaneous estimation of orbit and atmospheric density with a sequential estimator where use is made of tracking data before the state epoch and tracking data after the state epoch. This is enabled with VLS. A third example is provided by the optimal GPS orbit determination and time-transfer problem using GPS pseudo-range measurements and GPS carrier-phase measurements, where carrier-phase range-biases must be estimated at fixed epochs. This is enabled with VLS. These examples demonstrate the need for VLS.

As previously discussed, using an EKF that runs forward with time followed by an extended FIS that runs backward with time does not provide near-real-time estimation because all measurements of interest across the fixed-interval must be completely filtered and smoothed before an FIS state estimate is available for use. What would useful is a Class Ã estimator that runs forward with time, provides near-real-time throughput, improves estimation accuracy significantly relative to the EKF due to smoothing, and can process time-variable lags.

One approach to achieving a near-real-time nonlinear estimator with improved accuracy is to extend Class A filter-smoothers to Class Ã filter-smoothers. Table 1 identifies five known linear estimators that are candidates for extension to non-linear estimators. These estimators have properties summarized in Table 2.

TABLE 1

CLASS A
LINEAR SEQUENTIAL ESTIMATORS

| Class A (Linear Estimator) | Acronym |
| --- | --- |
| Kalman Filter | KF |
| Fixed Interval Smoother | FIS |
| Fixed Epoch Smoother/Carlton-Rauch | FES/CR |
| Fixed Epoch Smoother/Fraser | FES/F |
| Fixed Lag Smoother | FLS |

TABLE 2

AVAILBLE PROPERTIES OF LINEAR ESTIMATORS

| Class A (Linear Estimator) | KF | FIS | FES/CR | FES/F | FLS |
| --- | --- | --- | --- | --- | --- |
| Initial Conditions | user | terminal KF | KF at FE | KF at FE | after KF-FIS |
| Time Direction | forward | backward | forward | forward | forward |
| Throughput | real-time | after KF-FIS | near-real-time | near-real-time | near-real-time |
| Matrix Inverses | 0 | 1 | 1 | 0 | 3 |
| Extension φ | yes | yes | no | no | no |
| Extension Φ | yes | yes | yes | yes | yes |

State estimates of linear algorithms are propagated with a linear transition matrix function Φ. It is important to note that extension of an algorithm from linear to non-linear can be achieved with two very different techniques. In the first technique, variations of the state estimate with a linear transition are propagated with the matrix function Φ. It appears that this can always be achieved. In the second technique, the state estimate is propagated directly with a nonlinear transition function φ. It appears that this cannot always be achieved with sequential smoothers.

Extension φ of Table 2 refers to an acceptable conversion of every linear propagation of state estimate to nonlinear numerical integration, for extension from Class A to Class Ã. Numerical integration φ for extension of KF and FIS algorithms are known. Numerical integration φ for extension of FES/CR, FES/F and FLS algorithms has not been demonstrated.

Extension Φ of Table 2 refers to the acceptable use of a linear transition matrix function Φ to propagate state estimate variations, rather than state estimates, for extension of the listed algorithms from Class A to Class Ã. In an embodiment, a linear transition matrix is used in conjunction with an FES/CR algorithm to propagate state estimate variations. In another embodiment, the EKF measurement residual is propagated linearly in conjunction with use of the FES/F algorithm.

The algorithms identified in Tables 1 and 2 were evaluated to determine whether they could be adapted for use with variable time-lag. The FLS algorithm does not meet this criterion. Also, the FLS algorithm is undesirable because it requires the calculation of three state-sized matrix inverses.

In embodiments described below, both the FES/CR and the FES/F are used in conjunction with an EKF to provide a variable lag smoother (VLS).

A. The Kalman Filter

In the classic linear Kalman filter algorithm there is no time-lag; the Kalman filter is a real-time mathematical algorithm. We present no embodiment of the linear Kalman filter. Rather, the linear Kalman filter algorithm serves as theoretical foundation for extension to the nonlinear EKF to be embodied.

1. Time Update

Linear

Let $t_k$ be the time of last measurement. The Kalman filter linear algorithm is set forth below. The following are known:
  n×1 matrix state estimate $\hat{X}_{k|k}$;
  n×n matrix state estimate error covariance matrix $P_{k|k}$;
  n×p disturbance transition matrix $\Gamma_{k+1,k}$;
  p×p process noise covariance matrix $Q_k$; and
  new measurement $y_{k+1}$ at time $t_{k+1} > t_k$.

The propagated state estimate $\hat{X}_{k+1|k}$ and covariance $P_{k+1|k}$ are then calculated:

$$\hat{X}_{k+1|k} = \Phi_{k+1,k} \hat{X}_{k|k} \tag{1}$$

$$P_{k+1|k} = \Phi_{k+1,k} P_{k|k} \Phi_{k+1,k}^T + \Gamma_{k+1,k} Q_k \Gamma_{k+1,k}^T \tag{2}$$

Non-Linear

In an embodiment, an extended Kalman filter (EKF) Time Update is performed. State estimate propagation is nonlinear, so the linear propagation $\Phi_{k+1,k} \hat{X}_{k|k}$ of Equation 1 is replaced with a numerical integrator $\phi\{\cdot\}$ as follows:

$$\hat{X}_{k+1|k} = \phi\{t_{k+1}; \hat{X}_{k|x}, t_k, u(\hat{X}(\tau|t_k), \tau), t_{k+1} \leq \tau \leq t_k\} \tag{3}$$

and the propagation $\Gamma_{k+1,k} Q_k \Gamma_{k+1,k}^T$ of white noise covariance $Q_k$ is replaced with a physically connected non-white noise covariance $P_{k+1,k}^{ff}$:

$$P_{k+1|k} = \Phi_{k+1,k} P_{k|k} \Phi_{k+1,k}^T + P_{k+1,k}^{ff} \tag{4}$$

where $P_{k+1,k}^{ff}$ is composed of a sum of doubly integrated acceleration error covariance functions due to gravity, air-drag, solar pressure, and thrusting.

2. Measurement Update

Linear

Let $t_k$ be the time of last measurement $y_k$. Given a new scalar measurement $y_{k+1}$ at time $t_{k+1} > t_k$, its non-zero measurement error covariance $R_{k+1}$, the propagated state estimate $\hat{X}_{k+1|k}$, and the propagated state estimate error covariance matrix $P_{k+1|k}$, and the measurement-state 1×n row matrix $H_{k+1}$, calculate:

$$\Delta y_{k+1|k} = y_{k+1} - H_{k+1} \hat{X}_{k+1|k} \tag{5}$$

$$\tilde{R}_{k+1} = H_{k+1} P_{k+1|k} H_{k+1}^T + R_{k+1} \tag{6}$$

$$K_{k+1} = P_{k+1|k} H_{k+1}^T \tilde{R}_{k+1|k}^{-1} \tag{7}$$

$$\hat{X}_{k+1|k+1} = \hat{X}_{k+1|k} + K_{k+1} \Delta y_{k+1|k} \tag{8}$$

$$P_{k+1|k+1} = (I - K_{k+1} H_{k+1}) P_{k+1|k} \tag{9}$$

Nonlinear

Class Ã algorithms utilize the nonlinear measurement representation $y(\hat{X}_{k+1|k})$ and calculations:

$$H_{k+1} = \left[\frac{\partial y(X)}{\partial X}\right]_{\hat{X}_{k+1|k}} \quad (10)$$

$$\Delta y_{k+1|k} = y_{k+1} - y(\hat{X}_{k+1|k}) \quad (11)$$

But calculations for $\tilde{R}_{k+1}$, $K_{k+1}$, $\hat{X}_{k+1|k+1}$, and $P_{k+1|k+1}$ have the same form as for Class A algorithms:

$$\tilde{R}_{k+1} = H_{k+1} P_{k+1|k} H_{k+1}^T + R_{k+1} \quad (12)$$

$$K_{k+1} = P_{k+1|k} H_{k+1}^T \tilde{R}_{k+1}^{-1} \quad (13)$$

$$\hat{X}_{k+1|k+1} = \hat{X}_{k+1|k} + K_{k+1} \Delta y_{k+1|k} \quad (14)$$

$$P_{k+1|k+1} = (I - K_{k+1} H_{k+1}) P_{k+1|k} \quad (15)$$

B. Carlton-Rauch Fixed-Epoch Smoother

The mathematical specification an embodiment using a Carlton-Rauch fixed-epoch smoother is presented below.

1. FES Initialization

Let $t_{FE}$ denote a fixed epoch, coincident with time centroid of an impulsive spacecraft maneuver and known a priori. Let $\hat{X}_{FE}$ and $P_{FE}$ denote filtered state estimate and covariance at $t_{FE}$. In the prior art presentation of the Carlton-Rauch FES, $t_{FE}$ is denoted as coincident with time-tag of some measurement processed; i.e., $t_{FE} = t_k$ for $\hat{X}_{FE} = \hat{X}_{k|k}$ and $P_{FE} = P_{k|k}$, but this is not necessary. It may be necessary that $\hat{X}_{FE} = \hat{X}_{k|k-1}$ and $P_{FE} = P_{k|k-1}$ for propagated state estimate $\hat{X}_{k|k-1}$ and covariance $P_{k|k-1}$. However, for ease of discussion, the prior art notation will be used.

Let $\hat{X}_{k|j-1}$ denote an FES state estimate with fixed epoch $t_k$ where $j=k+1$, where the last measurement processed by the filter has time-tag $t_k$ or $t_{k-1}$, and where $t_k \leq t_{j-1}$ or $t_{k-1} \leq t_{j-1}$ respectively. With the filter at time $t_{FE} = t_k$, initialize the FES by storing objects associated with, or calculated by, the filter. Store $t_k$ and $$\hat{X}_{k|j-1} = \hat{X}_{FE}; \quad (16)$$

$$P_{k|j-1} = P_{FE}; \quad (17)$$

$$\hat{X}_{j-1|j-1} = \hat{X}_{FE}; \quad (18)$$

$$P_{j-1|j-1} = P_{FE}; \text{ and} \quad (19)$$

$$B_{j-1} = I. \quad (20)$$

2. Measurement at $t_j = t_{k+1}$

For this section $j=k+1$, where $t_k$ is the fixed epoch and $t_j > t_k$ is the time-tag for a new measurement $y_j = y_{k+1}$.

Filter

The filter calculates the propagated state estimate $\hat{X}_{k+1|k} = \hat{X}_{j|j-1}$, propagated covariance $P_{k+1|k} = P_{j|j-1}$, filtered state estimate $\hat{X}_{k+1|k+1} = \hat{X}_{j|j}$, filtered covariance $P_{k+1|k+1} = P_{j|j}$, and transition matrix $\Phi_{k+1,k} = \Phi_{j,j-1}$. Store $\hat{X}_{j|j-1}$, $P_{j|j-1}$, $\hat{X}_{j|j}$, $P_{j|j}$ and $\Phi_{j,j-1}$ for use in the FES. For the first value of $B_j$, following FES initialization, set $$B_j = B_{j-1} A_{j-1} \quad (21)$$

where $$A_{j-1} = P_{j-1|j-1} \Phi_{j,j-1}^T P_{j|j-1}^{-1} \quad (22)$$

FES

FES calculations refer to the fixed epoch $t_k$, and to filter measurement time-tags $t_j \geq t_k$.

$$\hat{X}_{k|j} = \hat{X}_{k|j-1} + B_j [\hat{X}_{j|j} - \hat{X}_{j|j-1}] \quad (23)$$

$$P_{k|j} = P_{k|j-1} + B_j [P_{j|j} - P_{j|j-1}] B_j^T \quad (24)$$

If the column matrix $\hat{X}_{k|j}$ has n elements, then $P_{k|j}$, $P_{k|j-1}$, $P_{j|j-1}$, $P_{j|j}$, $B_j$, and $\Phi_{j,j-1}^T$ are n×n matrices. Covariance matrices $P_{k|j}$, $P_{k|j-1}$, $P_{j|j-1}$, $P_{j|j}$, are symmetric and are free of negative eigenvalues. Zero eigenvalues in $P_{j|j-1}$ are not acceptable because it must be inverted. The implementation must guarantee that symmetric matrices are numerically symmetric, that all covariance matrices are numerically free of negative eigenvalues, and that $P_{j|j-1}$ is free of zero eigenvalues.

Filter

After FES execution and recording of FES results, the FES recursion is performed by the filter in preparation for the next measurement.

$$\hat{X}_{k|j-1} = \hat{X}_{k|j} \quad (25)$$

$$P_{k|j-1} = P_{k|j} \quad (26)$$

$$B_{j-1} = B_j \quad (27)$$

3. Measurements at $t_j = t_{k+1}, t_{k-2} \ldots$

In the section Measurement at $t_j = t_{k+1}$ above, replace $t_{k+1}$ with $t_{k+2}$ for the measurement at $y_j = y_{k+2}$ at time $t_{k+2}$. When $t_j = t_{k+h}$, replace $t_{k+1}$ with $t_{k+h}$ for the measurement $y_j = y_{k+h}$ at time $t_{k+h}$.

C. Fraser Fixed-Epoch Smoother

The mathematical specification for an embodiment using a Fraser fixed-epoch smoother is presented below.

1. FES Initialization

Let $t_{FE}$ denote a fixed epoch, coincident with time centroid of an impulsive spacecraft maneuver and known a priori. Let $\hat{X}_{FE}$ and $\hat{P}_{FE}$ denote filtered state estimate and covariance at $t_{FE}$. In the prior art presentation of the Fraser FES $t_{FE}$ is denoted as coincident with time-tag of some measurement processed; i.e., $t_{FE} = t_k$ for $\hat{X}_{FE} = \hat{X}_{k|k}$ and $P_{FE} = P_{k|k}$, but this is not necessary. It may be necessary that $\hat{X}_{FE} = \hat{X}_{k|k-1}$ and $P_{FE} = P_{k|k-1}$ for propagated state estimate $\hat{X}_{k|k-1}$ and covariance $P_{k|k-1}$. However, for ease of discussion, the prior art notation will be used.

Let $\hat{X}_{k|j-1}$ denote an FES state estimate with fixed epoch $t_k$ where $j=k+1$, where the last measurement processed by the filter has time-tag $t_k$ or $t_{k-1}$, and where $t_k \leq t_{j-1}$ or $t_{k-1} \leq t_{j-1}$ respectively. With the filter at time $t_{FE} = t_k$, initialize the FES by storing objects associated with, or calculated by, the filter: $t_k$, $\hat{X}_{k|j-1} = \hat{X}_{FE}$, $P_{k|j-1} = P_{FE}$, and $W_{j-1} = P_{FE}$.

2. Measurement at $t_j = t_{k+1}$

For this section, $j=k+1$, where $t_k$ is the fixed epoch and $t_j > t_k$ is the time-tag for a new measurement $y_j = y_{k+1}$.

Filter

The filter calculates the propagated state estimate $\hat{X}_{k+1|k} = \hat{X}_{j|j-1}$, propagated covariance $P_{k+1|k} = P_{j|j-1}$, filtered state estimate $\hat{X}_{k+1|k+1} = \hat{X}_{j|j}$, filtered covariance $P_{k+1|k+1} = P_{j|j}$, transition matrix $\Phi_{k+1,k} = \Phi_{j,j-1}$, measurement-state jacobian matrix $H_{k+1} = H_j$, measurement covariant matrix $R_{k+1} = R_j$, and measure residual $\Delta y_{k+1,k} = \Delta y_{j,j-1}$ at time tag $t_{k+1} = t_j$ for the new measurement $y_{k+1} = y_j$. Store $\hat{X}_{j|j-1}$, $P_{j|j-1}$, $\hat{X}_{j|j}$, $P_{j|j}$, $\Phi_{j|j-1}$, $H_j$, $R_j$ and $\Delta y_{j,j-1}$ for use in the FES.

FES

FES calculations refer to the fixed epoch $t_k$, and to filter measurement time-tags $t_j \geq t_k$.

$$S_j = H_j^T R_j^{-1} H_j \quad (28)$$

$$W_j = W_{j-1} \Phi_{j,j-1}^T [I - S_j P_{j|j}] \quad (29)$$

$$\hat{X}_{k|j} = \hat{X}_{k|j-1} + W_j H_j^T R_j^{-1} \Delta y_{j,j-1} \quad (30)$$

$$P_{k|j} = P_{k|j-1} - W_j [S_j P_{j|j-1} S_j + S_j] W_j^T \quad (31)$$

If the column matrix $\hat{X}_{k|j}$ has n elements, then $P_{k|j}$, $P_{k|j-1}$, $P_{j|j-1}$, $P_{j|j}$, $\Phi_{j,j-1}^T$, $S_j$, and $W_j$ are n×n matrices. Covariance matrices $P_{k|j}$, $P_{k|j-1}$, $P_{j|j-1}$, $P_{j|j}$ are symmetric and are free of negative eigenvalues. Zero eigenvalues in $P_{j|j-1}$ are acceptable because no state-sized covariance matrix inverse is required for the Fraser form of the FES. $S_j$ is seen to be symmetric by inspection of its defining Equation 28. The implementation must guarantee that symmetric matrices are numerically symmetric and that covariance matrices are numerically free of negative eigenvalues. $W_{j-1}$ is initialized as a symmetric covariance matrix, but $W_j$ and $W_{j-1}$ subsequent are not symmetric due to the factor $\Phi_{j,j-1}^T$ in the recursive Equation 29.

FES calculations require products of matrices with extreme differences in order of magnitude. For example, the calculation of $W_j$ according to Equation 29 requires evaluation of the product $S_j P_{j|j}$ that is subtracted from a matrix of order unity. The eigenvalues of $S_j$ are very large due to the small values of $R_j$, and the eigenvalues of $P_{j|j}$ are very small, all non-negative. The product $S_j P_{j|j}$ is of order unity, but some significance is lost in double precision calculations. It may thus be advisable to premultiply $S_j$ by a small positive scalar $\epsilon$ and premultiply $P_{j|j}$ by its inverse $\epsilon^{-1}$ for calculation of the product $S_j P_{j|j} = (S_j \epsilon)(\epsilon^{-1} P_{j|j})$ where $S_j \epsilon$ and $\epsilon^{-1} P_{j|j}$ are both of order unity.

Filter

After FES execution and recording of FES results, the FES recursion is performed by the filter in preparation for the next measurement:

$$\hat{X}_{k|j-1} = \hat{X}_{k|j} \quad (32)$$

$$P_{k|j-1} = P_{k|j} \quad (33)$$

$$W_{j-1} W_j \quad (34)$$

3. Measurements at $t_j = t_{k+1}$, $t_{k+2}$ . . .

In the section "Measurement at $t_j = t_{k+1}$" above, replace $t_{k+1}$ with $t_{k+2}$ for the measurement at $y_j = y_{k+2}$ at time $t_{k+2}$. When $t_j = t_{k+h}$, replace $t_{k+1}$ with $t_{k+h}$ for the measurement $y_j = y_{k+h}$ at time $t_{k+h}$.

In an embodiment, a smoother window is anchored to each fixed epoch of an FES. Smoother window definition logic may be selected by the user at run-time. By way of illustration and not as a limitation, the selected window definition may establish a constant window length for each smoothing window. Alternatively, the user may select time-varying criteria that require satisfaction of accuracy thresholds by time-varying covariance matrix elements, together with maxima of smoother window length.

Figure 1:
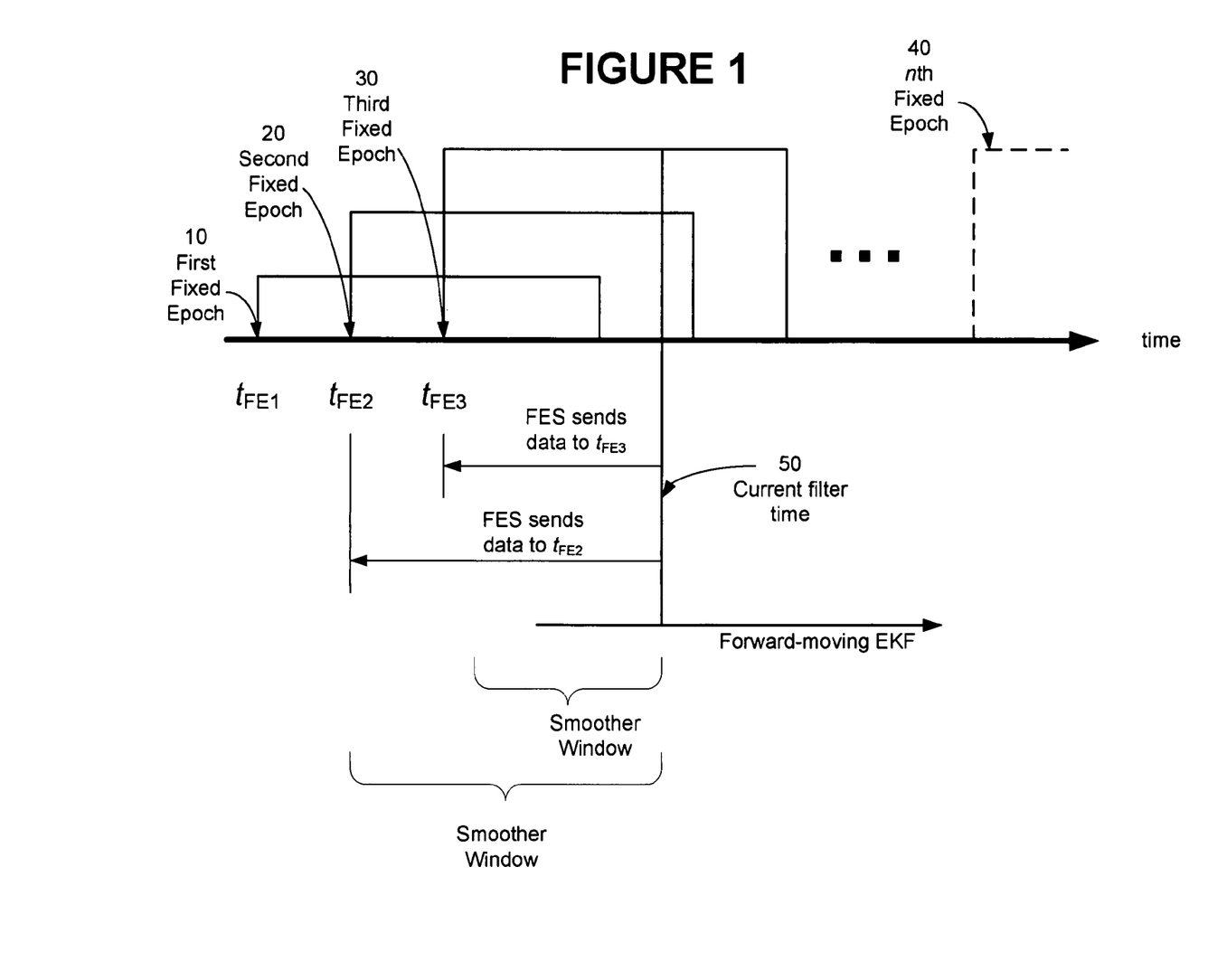
FIG. 1 illustrates a general application of variable lag smoother with fixed epochs on a uniform time grid according to an embodiment.

As illustrated in FIG. 1, the smoother windows are overlapping. However, this is not meant as a limitation. The smoother windows may, for example, be non-overlapping or established on a non-uniform time grid.

FIG. 1 illustrates a general application of variable lag smoother with fixed epochs on a uniform time grid according to an embodiment.

In this embodiment, a variable lag smoother utilizes a forward moving extended Kalman filter (EKF) and multiple fixed epoch smoother (FES) instances. As illustrated in FIG. 1, an EKF is operating at a point in time identified as EKF current time 50. EKF current time 50 moves on a time grid dictated by measurement time-tags, generally non-uniform.

A FES instance is associated with a time window. The FES instance operates for as long as the EKF current time is within the time window associated with that FES instance. As illustrated, the EKF current time 50 crosses second fixed epoch 20 and third fixed epoch 30. The output of the EKF is sent to FES$_2$ and FES$_3$. When the EKF reaches boundary of second fixed epoch 20, FES$_2$ is terminated and the associated smoother results are recorded. When the EKF current time 50 first reaches an FES boundary, such as the boundary of n-th epoch 40, a new FES instance is created and initialized.

For example, a variable lag smoother uses fixed epochs having one minute granularity and a window of 300 minutes in length. The FES sends EKF information backwards to the fixed epoch while the forward running EKF remains in the smoother window. Thus, the FES has a maximum lag from real-time of 300 minutes.

The FES estimate is initialized by the EKF estimate at the fixed epoch after all measurements have been processed by the EKF at the fixed epoch. As the EKF epoch window 50 moves forward, information derived from the EKF at each measurement time-tag is sent backwards to the fixed epoch by the FES while the EKF epoch is in the smoother window. The FES is invoked only for EKF measurement updates. The FES is not invoked for EKF time updates, unlike FIS operation. The lag of fixed epoch relative to the EKF epoch increases throughout passage of the EKF across the smoother window due to forward motion of the EKF epoch. The lag is thus characterized as variable and the estimator referred to as a variable lag smoother or VLS.

In an embodiment, When a VLS is terminated by a user with the EKF epoch inside of a smoother window, the user may optionally accept results of the VLS with partial completion of the last smoother window or save the results into an EKF restart file just prior to entry of the EKF epoch into the last smoothing window.

Impulsive Maneuvers Example

Consider a single spacecraft that performs impulsive maneuvers. Impulse maneuvers are used to model thrust intervals that are short in comparison to orbit period. The sequential estimation of the state from tracking measurements comprises six components of position and velocity, force model parameters, and time-varying measurement biases. By way of illustration and not as a limitation, other state parameters may include photon solar pressure, clock biases, spacecraft maneuver parameters, albedo acceleration, troposphere bias, ionosphere biases, station location biases, antenna phase center biases, and multi-path biases. A typical approach is to use a fixed interval smoother that provides an estimation that runs backward with time.

Figure 2:
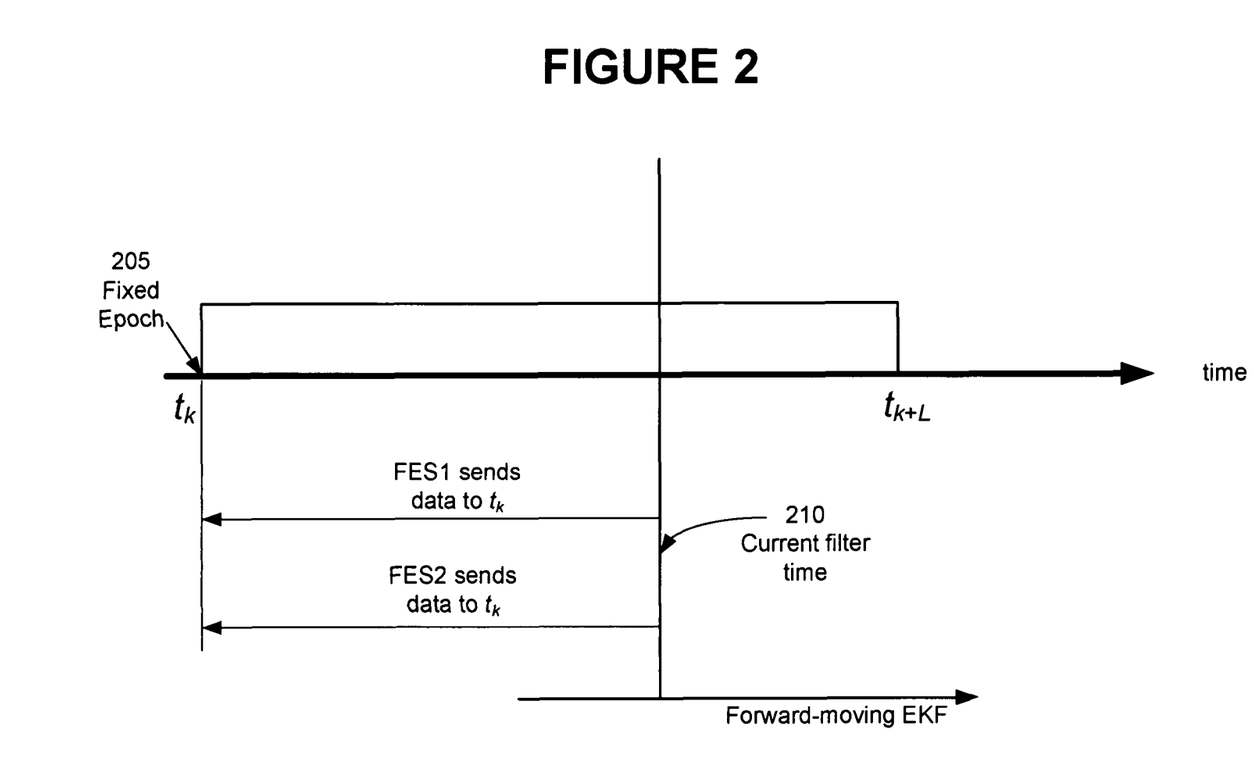
FIG. 2 illustrates an application a variable lag smoother to the estimation of velocity at a fixed epoch according to an embodiment.

FIG. 2 illustrates an application a variable lag smoother to the estimation of velocity at a fixed epoch according to an embodiment. In this embodiment, a VLS method eliminates the on-line FIS, uses a forward running EKF, and uses two FES smoothers that send EKF estimate information backwards from the current filter time 210 to a fixed epoch 205. The fixed epoch is defined by an impulsive maneuver time centroid, say $t_k$ as illustrated in FIG. 2.

Let $t_k$ denote the time centroid of an impulsive spacecraft maneuver. Let $\hat{X}_{k|i}^{(-)}$ and $P_{k|i}^{(-)}$ denote the state estimate and covariance derived by the EKF from processing the last measurement $y_i$ with time-tag $t_i \leq t_k$. The estimate $\hat{X}_{k|i}^{(-)}$ does not include addition of the velocity change at $t_k$, and its associated covariance matrix $P_{k|i}^{(-)}$ does not include the addition of EKF maneuver process noise covariance at $t_k$. The EKF state estimate $\hat{X}_{k|i}^{(-)}$ and covariance matrix $P_{k|i}^{(-)}$ are used to initialize FES1 at time $t_k$.

Let $\hat{X}_{k|i}^{(+)}$ and $P_{k|i}^{(+)}$ denote the state estimate and covariance derived after application of velocity change to $\hat{X}_{k|i}^{(-)}$, and after addition of maneuver process noise covariance to $P_{k|i}^{(-)}$. The state estimate $\hat{X}_{k|i}^{(+)}$ and covariance matrix $P_{k-i}^{(+)}$ are used to initialize FES2 at time $t_k$. A smoothing window $\{t_k, t_{k+L}\}$ is selected by the user, explicitly or implicitly. Now we process measurements $y_j$, $j=k+1; k+2, \ldots k+L$ by the EKF, and operate both FES1 and FES2 on the EKF output across the smoothing window $\{t_k, t_{k+L}\}$. The VLS with two FES smoothers produces smoothed estimates $\hat{X}_{k|k+L}^{(-)}$ and $\hat{X}_{k|k+L}^{(+)}$ and their covariance matrices $P_{k|k+L}^{(-)}$ and $P_{k|k+L}^{(+)}$. The desired estimate of velocity change is found in the velocity components of the difference $\hat{X}_{k|k+L}^{(+)} - \hat{X}_{k|k+L}^{(-)}$.

In an embodiment, a VLS is applied to estimate the impulse maneuvers of a hostile spacecraft, where the time centroids are initially unknown. In another embodiment, a VLS is extended to estimate finite (non-impulsive) maneuvers of friendly spacecraft and hostile spacecraft from tracking data.

Atmospheric Density Example

Figure 3:
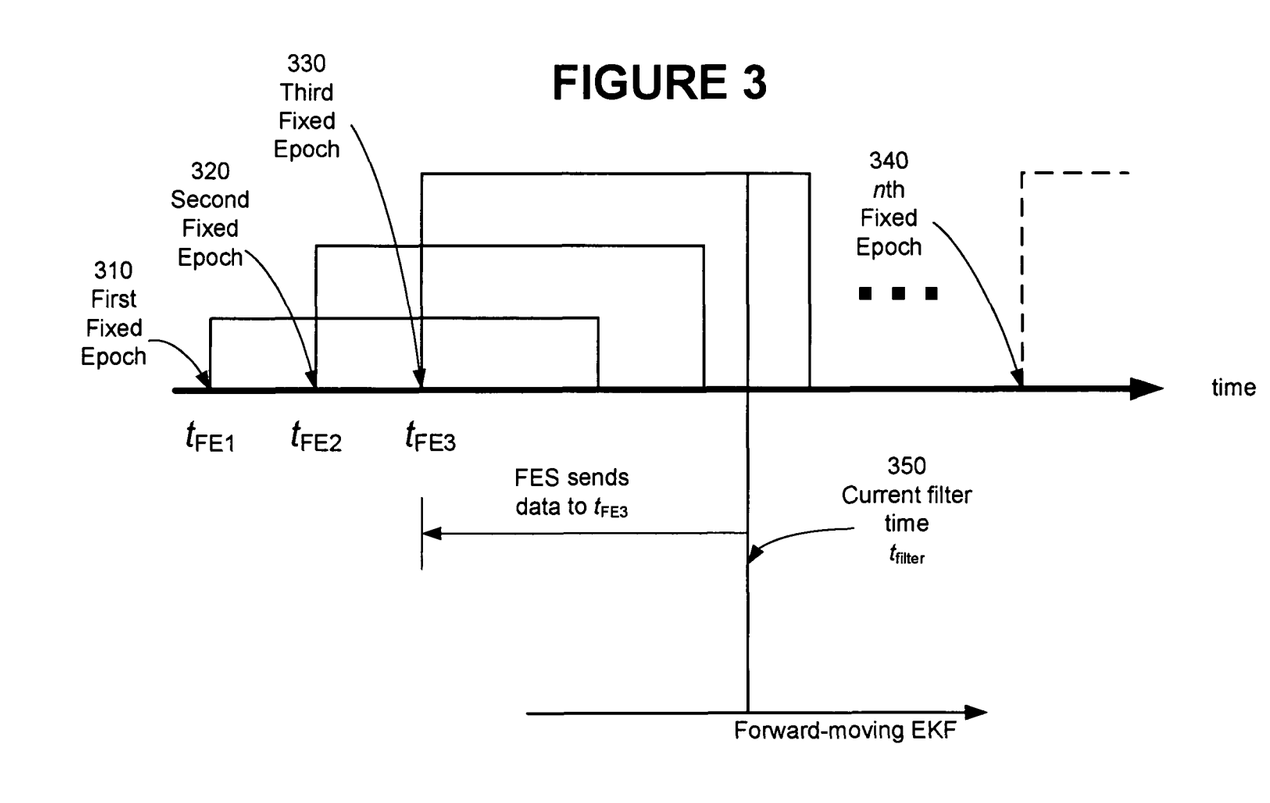
FIG. 3 illustrates an application a variable lag smoother to the estimation of orbits and global atmospheric density according to an embodiment.

FIG. 3 illustrates an application a variable lag smoother to the estimation of orbits and global atmospheric density according to an embodiment. Consider the simultaneous orbit determination of an ensemble of LEO spacecraft, together with estimation of atmospheric density and ballistic coefficient for each spacecraft, the estimation of global parameters of atmospheric density that drive a physically connected time-varying model, and the estimation of appropriate time-varying measurement biases.

Tracking data are received on all LEO spacecraft and are processed by the EKF as they are received. At run-time the user selects smoother windows that are anchored to fixed epochs $t_{FE1}$ 310, $t_{FE2}$ 320, $t_{FE3}$ 330, ... $t_{FEn}$ 340. When the time-varying EKF epoch $t_{filter}$ 350 reaches $t_{FEn}$, for n=1, 2, 3, ..., an FES is initialized there and the FES estimate of global atmospheric density is improved at $t_{FEn}$ until the EKF exits the $t_{FEn}$ smoothing window. The time-varying global atmospheric density model can be propagated forward from the last fixed epoch to provide optimal predictions of global atmospheric density with estimation error covariance.

GPS Carrier Phase Range Example

Figure 4:
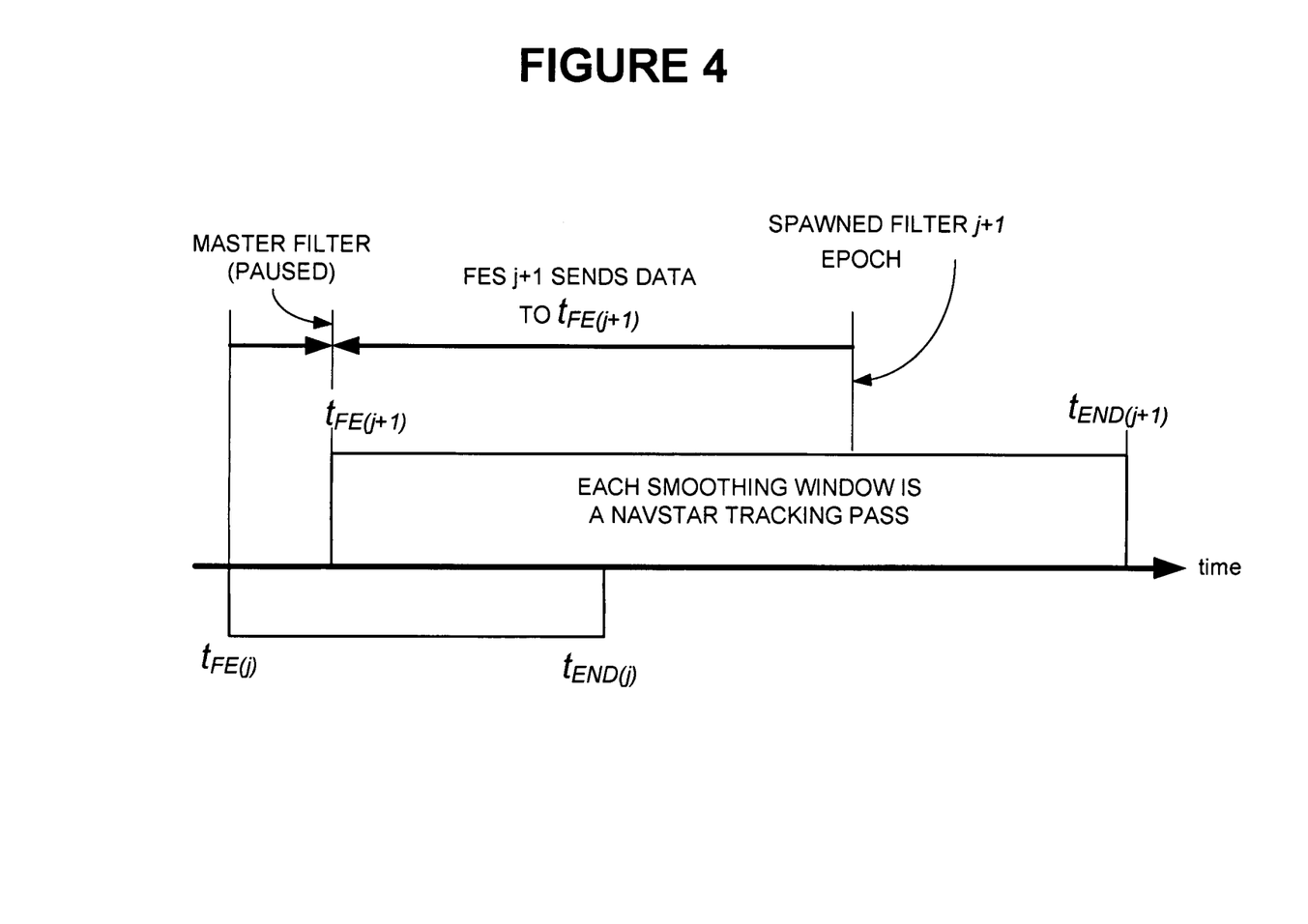
FIG. 4 illustrates an application a variable lag smoother to the estimation of carrier-phase-as-range-bias according to an embodiment.

FIG. 4 illustrates an application a variable lag smoother to the estimation of carrier-phase-as-range-bias according to an embodiment. The estimation of carrier phase range bias from ground station carrier phase measurements over phase count intervals of several hours, with the simultaneous processing of ground station pseudo-range measurements, enables the most accurate method for GPS time transfer. In this embodiment, GPS time transfer with GPS carrier phase measurements is realized in near-real-time using a VLS with an FES for each fixed epoch. Consider a GPS NAVSTAR constellation of N spacecraft, where we estimate n state parameters for each NAVSTAR spacecraft.

As illustrated in FIG. 4, a forward running EKF Master Filter (MF) with Nn state elements, two fixed epochs ($FE_j$ and $FE_{(j+1)}$) with two smoothing windows, a forward running EKF Spawned Filter (SF) with n+1 state elements for each smoothing window, and an FES with n+1 state elements for each fixed-epoch associated with each forward running SF. The Nn×1 column matrix state of the MF contains all NAVSTAR orbits, solar pressure parameters, and clock parameters. Each SF state and each FES state is an (n+1)×1 matrix with the same structure. The n×1 substrate matrix of each (n+1)×1 matrix is also a substrate of the MF state.

Each SF state and each FES state contains an element for a constant carrier-phase-as-range bias not contained in the MF state. State estimate and covariance for each SF and each FES are initialized at a fixed-epoch defined by the first carrier phase measurement for each NAVSTAR on a particular tracking data pass. The MF is paused at the fixed-epoch while the SF and FES operate across the smoothing window. The SF and FES exist for duration of the smoothing window defined by tracking data pass time interval. The (n+1)×1 matrix FES state is transformed to an n×1 matrix MF pseudo-measurement that is processed by the MF after the SF reaches the end of smoothing window. The SF and FES are destroyed at the end of each smoothing window. The MF continues and survives indefinitely.

In an embodiment, a VLS is used to perform near-real-time GPS time transfer, derived from a combination GPS pseudo-range measurements and GPS carrier-phase measurements. In another embodiment, a VLS is used to optimally and simultaneously estimate GPS NAVSTAR orbits, clocks, and carrier-phase range biases at fixed epochs from a combination GPS pseudo-range measurements and GPS carrier-phase measurements. This VLS is applicable to the US Air Force GPS real-time operations. The MF state estimate is propagated forward to real-time from the latest completed smoothing window. Superior orbit estimate accuracy is derived from use of GPS carrier-phase measurements and estimation of carrier-phase range biases.

It will be understood by those skilled in the art that the present invention may be embodied in other specific forms without departing from the scope of the invention disclosed and that the examples and embodiments described herein are in all respects illustrative and not restrictive. Those skilled in the art of the present invention will recognize that other embodiments using the concepts described herein are also possible. Further, any reference to claim elements in the singular, for example, using the articles "a," "an," or "the" is not to be construed as limiting the element to the singular. It should also be appreciated that functionality ascribed to a device circuit herein may be provided by instructions that are incorporated into the device or that are provided to the device in the form of a software program. Additionally, it should be understood that a device that is described as "adapted" to perform a particular function may perform the function as an inherent consequence of its design, by executing instructions, or by virtue of a configuration of the device.

What is claimed is:

1. A variable lag smoother comprising:
   an extended Kalman filter (EKF) configured to receive data over a time period and to provide data representative of an estimate of a state of a device, wherein the state comprises state parameters at a current time t within the time period; and
   a plurality of fixed epoch smoothers, wherein each fixed epoch smoother (FES) is in communication with the EKF and is configured to:
   operate within a time window defined by an epoch start time and an epoch stop time;
   receive data from the EKF beginning when the current time t is equal to the epoch start time and ending when the current time t is greater than the epoch stop time; and
   provide an updated estimate of the state of the device as of the epoch start time.

2. The variable lag smoother of claim 1, wherein the time windows of each of the plurality of FESs do not overlap.

3. The variable lag smoother of claim 1, wherein the time windows of each of the plurality of FESs overlap by a fixed amount of time.

4. The variable lag smoother of claim 1, wherein the time windows of each of the plurality of FESs is a fixed time interval.

5. The variable lag smoother of claim 1, wherein the epoch stop time is determined when a time-varying criterion is satisfied.

6. The variable lag smoother of claim 1, wherein the time-varying criterion comprises an accuracy threshold.

7. The variable lag smoother of claim 5, wherein the epoch stop time is determined by the earlier of when a time-varying criterion is satisfied and when a maximum time window threshold is satisfied.

8. The variable lag smoother of claim 1, wherein the FES is a Fraser fixed-epoch smoother.

9. The variable lag smoother of claim 1, wherein the FES is a Carlton-Rauch fixed-epoch smoother.

10. The variable lag smoother of claim 1, wherein the device comprises a spacecraft and the state parameters are selected from the group consisting of a spacecraft position, spacecraft velocity, atmospheric density, ballistic coefficient, photon solar pressure, clock biases, spacecraft maneuver parameters, albedo acceleration, troposphere bias, ionosphere biases, station location biases, antenna phase center biases, multi-path biases and measurement biases.

11. A method of estimating a state of a device comprising:
configuring an extended Kalman filter (EKF) to receive data over a time period and to provide data representative of an estimate of a state of the device, wherein the state comprises state parameters at a current time within the time period; and
configuring a plurality of fixed epoch smoothers, wherein each fixed epoch smoother (FES) is in communication with the EKF and is configured to:
operate within a time window defined by an epoch start time and an epoch stop time;
receive data from the EKF beginning when the current time t is equal to the epoch start time and ending when the current time t is greater than the epoch stop time; and
provide an updated estimate of the state of the device as of the epoch start time.

12. The method of claim 11, wherein the time windows of each of the plurality of FESs do not overlap.

13. The method of claim 11, wherein the time windows of each of the plurality of FESs overlap by a fixed amount of time.

14. The method of claim 11, wherein the time windows of each of the plurality of FESs is a fixed time interval.

15. The method of claim 11 wherein the epoch stop time is determined when a time-varying criterion is satisfied.

16. The method of claim 11, wherein the time-varying criterion comprises an accuracy threshold.

17. The method of claim 15, wherein the epoch stop time is determined by the earlier of when a time-varying criterion is satisfied and when a maximum time window threshold is satisfied.

18. The method of claim 11, wherein the FES is a Fraser fixed-epoch smoother.

19. The method of claim 11, wherein the FES is a Carlton-Rauch fixed-epoch smoother.

20. The method of claim 11, wherein the device comprises a spacecraft and the state parameters are selected from the group consisting of a spacecraft position, spacecraft velocity, atmospheric density, ballistic coefficient, photon solar pressure, clock biases, spacecraft maneuver parameters, albedo acceleration, troposphere bias, ionosphere biases, station location biases, antenna phase center biases, multi-path biases and measurement biases.

* * * * *